United States Patent
Edic et al.

(10) Patent No.: US 6,324,243 B1
(45) Date of Patent: Nov. 27, 2001

(54) METHOD AND APPARATUS FOR RECONSTRUCTING IMAGES FROM PROJECTION DATA ACQUIRED BY A COMPUTED TOMOGRAPHY SYSTEM

(75) Inventors: Peter Michael Edic, Albany; Ahmad Nadeem Ishaque; Mehmet Yavuz, both of Clifton Park, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/511,678

(22) Filed: Feb. 23, 2000

(51) Int. Cl.$^7$ ............................................. A61B 6/03
(52) U.S. Cl. ................................ 378/4; 378/8; 378/901
(58) Field of Search ........................ 378/4, 8, 15, 901

(56) References Cited

U.S. PATENT DOCUMENTS 5,640,462 * 6/1997 Sato et al. ........................... 382/131

5,930,330 * 7/1999 Wolfe et al. ........................ 378/98.2

\* cited by examiner

*Primary Examiner*—David V. Bruce
(74) *Attorney, Agent, or Firm*—Donald S. Ingraham; Christian G. Cabou

(57) ABSTRACT

A method and apparatus for use with a volumetric computed tomography (CT) scanning system. In accordance with the present invention, the volumetric CT scanning system utilizes an area detector to acquire projection data. The acquired projection data is stored in memory. The projection data corresponding to groups of pixels of the detector is then rebinned to thereby reduce the amount of projection data that will be utilized in performing an initial volumetric reconstruction of the image. The reconstructed image may then be processed to identify particular regions of interest, such as a pathology. If a particular region of interest is identified, all of the projection data corresponding to the region is then used to retrospectively reconstruct a high resolution image of the region of interest. The retrospectively reconstructed high resolution image can then be processed and analyzed to further evaluate the region of interest.

37 Claims, 3 Drawing Sheets

METHOD AND APPARATUS FOR RECONSTRUCTING IMAGES FROM PROJECTION DATA ACQUIRED BY A COMPUTED TOMOGRAPHY SYSTEM

BACKGROUND OF THE INVENTION

The invention relates to computed tomography (CT) and, more particularly, to an apparatus and a method for use in a volumetric CT scanning system for reconstructing images.

Computed tomography (CT) is a technique that generally involves subjecting a patient to x-rays, acquiring digital x-ray projection data of a portion of the patient's body, and processing and back-projecting the digital x-ray projection data to produce an image that is then displayed on a display monitor of the CT system. CT systems typically comprise a gantry, a table, an x-ray tube, an x-ray detector array, a computer and a display monitor. The computer sends commands to controllers of the gantry to cause the controllers to rotate the x-ray tube and/or the detector array at a particular rotational speed. The detector array is usually comprised of either a curved array (third generation CT system) of detector elements or a ring (fourth generation CT system) of detector elements. In the case where a ring of detector elements is used, only the x-ray tube is rotated.

In third and fourth generation CT systems, relative rotational motion is produced between the detector array and the x-ray tube about the patient's body. As this relative rotational motion is produced, the computer controls the data acquisition process performed by the x-ray tube and the detector array to acquire digital x-ray radiographs. The computer then processes and back-projects the digital x-ray radiograph data by performing a reconstruction algorithm and displays the reconstructed CT image on the display monitor.

In medical screening applications, dose delivered to the patient is always of great concern. To minimize risk to the patient, the dose delivery by diagnostic imaging procedures is minimized. This is especially true when the diagnostic procedures are utilized for screening applications. In general, lower dose, lower resolution CT data are acquired in the initial screening examination. However, if some pathology is observed, such as a solitary lung nodule observed during a thoracic imaging procedure, the patient is normally required to return to the hospital for an additional high-dose, high-resolution CT procedure. The administered radiation places the patient at higher risk and reduces the productivity of the hospital since the patient is required to make a follow-up visit.

In CT systems that utilize area detectors, the CT scanning procedure is known as volumetric CT scanning because CT data i; acquired by the area detector for a volume of the patient. By using high resolution area detectors in a volumetric CT scanning system, it is possible to reconstruct spatial volume data at extremely high resolution. In some cases, the resolution may be an order of magnitude higher than the resolution obtained with other types of detectors. Volumetric CT scanning enables diagnostic procedures to be performed quicker than with other types of CT scanning, which facilitates patient throughput for the hospital.

However, manipulating data at this higher resolution is generally prohibitive due to the long reconstruction times and the physical size of the reconstructed volume. High resolution area detectors have such a large number of pixels that the amount of data collected is extremely large, which presents problems in terms of storing, retrieving and manipulating the data in real time. It would be beneficial if a volumetric CT scanning system could be used to generate a relatively low resolution volumetric image that could be processed to identify potentially problematic areas. It would also be beneficial if a high resolution image of the area identified as being potentially problematic could be reconstructed. In this manner, the benefits of using a high resolution area detector could be realized, but not at the expense of reconstruction time or data storage/manipulation. Furthermore, if all of the data needed to generate the high and low resolution images could be acquired during a single scan of the patient, the patient would not be required to revisit the hospital, which could improve the productivity of the clinical environment. In addition, the radiation dose that is administered to the patient would be reduced, thus reducing the risk to the patient.

Accordingly, a need exists for a method and apparatus for use in a volumetric CT scanning system that reduces the amount of data that is used in initially reconstructing the image, but which utilizes all of the acquired data associated with a particular region of interest to retrospectively reconstruct a high resolution image of the region of interest. The initially reconstructed image would contain sufficient contrast information to enable certain problematic areas to be identified. The retrospectively reconstructed high resolution image of the problematic area could then be processed and analyzed to further evaluate the problematic area.

BRIEF SUMMARY OF THE INVENTION

The present invention provides a method and apparatus for use with a computed tomography (CT) system. In accordance with the present invention, the CT scanning system utilizes a detector, preferably an area detector, to acquire projection data. The acquired projection data is stored in memory. The projection data corresponding to groups of pixels of the detector is then rebinned to reduce the amount of projection data that will be utilized in performing an initial volumetric reconstruction of the image. The reconstructed image may then be processed to identify particular regions of interest, such as a pathology. Once a particular region of interest has been identified, all of the projection data corresponding to the region is used to retrospectively reconstruct a high resolution image of the region of interest. The retrospectively reconstructed high resolution image can then be processed and analyzed to further evaluate the region of interest.

These and other features and advantages of the present invention will become apparent from the following description, drawings and claims.

DETAILED DESCRIPTION OF THE INVENTION

Figure 1:
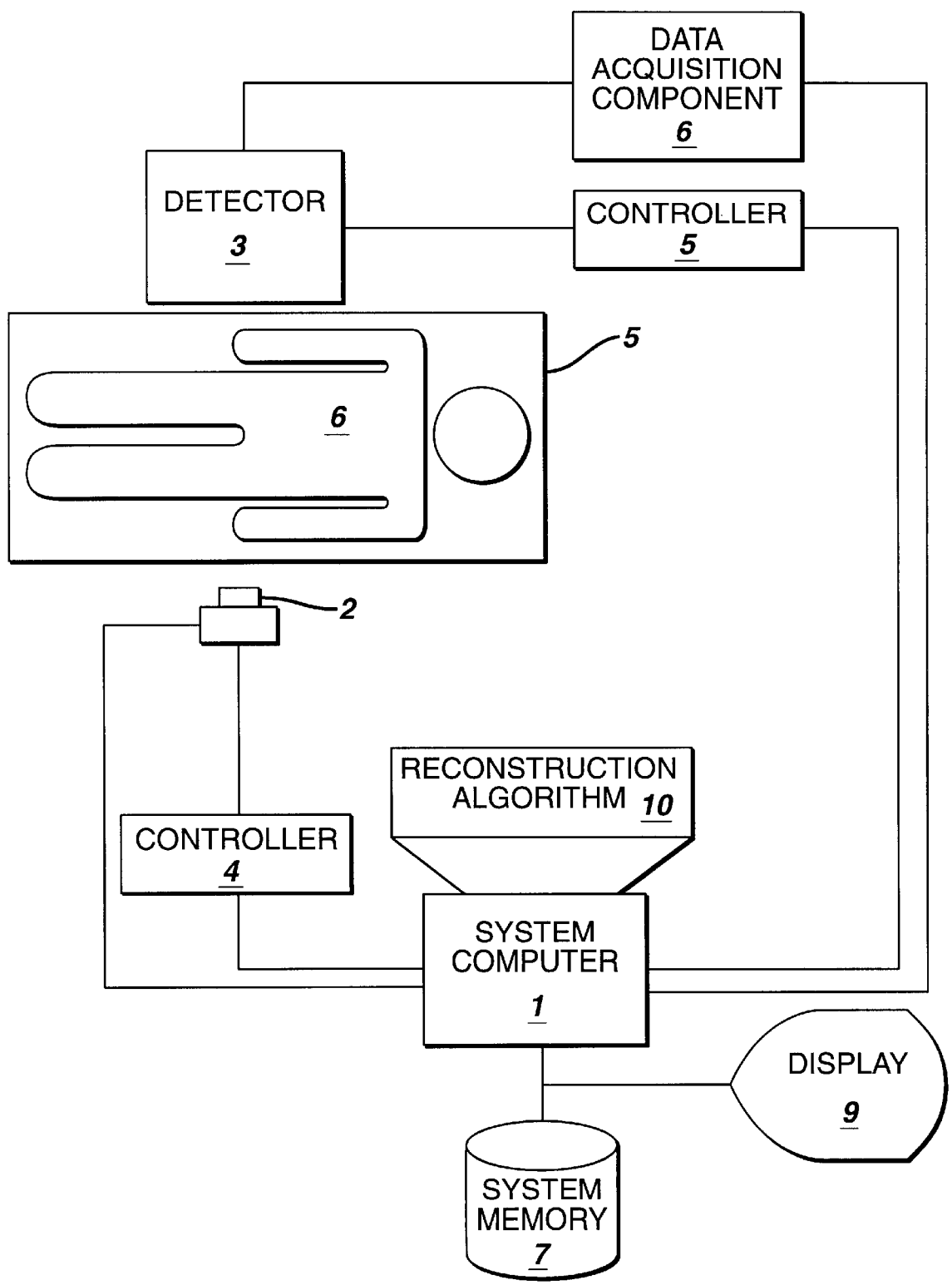
FIG. 1 is a block diagram illustrating the volumetric CT scanning system of the present invention in accordance with the preferred embodiment.

FIG. 1 is a block diagram of a volumetric CT scanning system that is suitable for implementing the method and apparatus of the present invention. The Volumetric CT scanning system will be discussed with respect to its use in reconstructing an image of an anatomical feature of a patient, although it will be understood that the present invention is not limited to imaging any particular object. The present invention may also be used for industrial processes, as will be understood by those skilled in the art.

In a volumetric CT scanning system, the gantry is rotated about an object, such as a human patient, and projection data is acquired. A computer 1 controls the operations of the volumetric CT scanning system. When referring herein to the rotation of the gantry, that phrase is intended to denote rotation of the x-ray tube 2 and/or rotation of the detector 3, which preferably is a high resolution area detector. The x-ray tube 2 and the detector 3 are comprised by the gantry. The controllers 4 and 5 are controlled by the Volumetric CT scanning system computer 1 and are coupled to the x-ray tube 2 and to the detector 3, respectively. The controllers 4 and 5 cause the appropriate relative rotational motion to be imparted to the x-ray tube 2 and/or to the detector 3. Individual controllers are not necessary. A single controller component may be used to rotate the gantry.

The computer 1 controls the data acquisition process by instructing the data acquisition component 6 as to when to sample the detector 3. The detector 3 is comprised of an array of pixels. Each pixel has an intensity value associated therewith that is related to the amount of x-ray energy that impinges on the pixel. During the data acquisition process, the computer 1 receives the acquired projection data from the data acquisition component 6 and stores the projection data at locations in the memory device 7. The projection data is in the form of radiographs. In accordance with the present invention, each radiograph is rebinned using one of the techniques described below with reference to FIGS. 3 and 4. The rebinning process reduces the amount of data that will be used to perform an initial, or first, reconstruction of the image. The rebinning process essentially is a low-pass filtering process that removes detail from the reconstructed image. However, the reconstructed image generally will contain as much resolution as images reconstructed by known CT scanning systems that use linear detector arrays and detector arrays comprising a few rows of pixels. Therefore, the reconstructed image contains a sufficient amount of information to be useful. For example, high contrast features will remain in the reconstructed image.

After this initial reconstruction of the image has been performed, the reconstructed image can be processed to identify areas of interest (e.g., nodules or other abnormalities). Such processing to identify areas of interest may be visualization by a human or by using automated detector techniques (e.g., algorithms to differentiate imaging representations of cancerous and normal tissue). Processing techniques exist that enable the reconstructed image to be processed by a computer to identify particular features of interest. Those skilled in the art will understand the manner in which such techniques can be employed. Also, processing techniques that are developed in the future may be suitable for analyzing the reconstructed image. The present invention is not limited with respect to the processing techniques that are described above.

In accordance with the present invention, if a particular feature of interest is identified, the projection data stored in the memory device 7 that corresponds to the region of interest will be read out of the memory device 7 and retrospectively reconstructed using the necessary projection data. Therefore, the retrospectively reconstructed image will have very high resolution. However, since only the projection data corresponding to the region of interest is utilized, the aforementioned difficulties associated with reconstruction time and data storage/manipulation are minimized or are not encountered at all. This retrospectively reconstructed image may then be processed in a manner similar to that discussed above to evaluate the region of interest.

The apparatus of the present invention is comprised of a computer that is capable of being configured to perform the reconstruction algorithm of the present invention, and a memory device. It should be noted that it is not necessary that the computer and memory device that are used to perform the reconstruction algorithm 10 be the computer 1 and memory device 7 that are utilized for the overall operations of the CT scanning system. For purposes of explanation, it will be assumed that the apparatus of the present invention is comprised of the computer 1 and the memory device 7 of the CT scanning system. The computer 1 may comprise one or more microprocessors, for example. The memory device comprised by the apparatus of the present invention may be separate from the microprocessor(s) or it may be on-board memory contained on the microprocessor(s). The memory device is not limited to any particular type of memory device. Preferably, the memory device is a solid state memory device, but it may also be, for example, a CD ROM, magnetic disk, magnetic tape, etc., or any other suitable computer-readable medium.

When the apparatus of the present invention is incorporated into a volumetric CT scanning system and is used in conjunction with the reconstruction algorithm 10 of the present invention, a new volumetric CT scanning system is created. Therefore, the present invention also provides a new volumetric CT scanning system.

It should also be noted that the present invention is not limited to any particular computer for performing the data acquisition and processing tasks of the present invention. The term "computer", as that term is used herein, is intended to denote any machine capable of performing the calculations, or computations, necessary to perform the tasks of the present invention. Therefore, the computer utilized to perform the reconstruction algorithm 10 of the present invention may be any machine that is capable of performing the necessary tasks.

A number of CT reconstruction algorithms are suitable for computing the initial and retrospective reconstructions. The CT reconstruction algorithm 10 utilized for this purpose can be a known CT reconstruction algorithm or a proprietary CT reconstruction algorithm. The CT reconstruction algorithm 10 does not need to be modified to handle the interpolated radiographs. A single reconstruction algorithm can be used to perform both reconstructions since the only difference between these reconstructions is the amount of data processed.

The well known Feldkamp algorithm is suitable for these purposes. The Feldkamp algorithm is disclosed in an article entitled "Practical Cone-Beam Algorithm," by L. Feldkamp, L. Davis and J. Kress, J. Opt. Soc. Am., A/Vol. 1, No. 6, June 1984. This algorithm is also disclosed in a text book entitled "Principles of Computerized Tomographic Imaging", by A. Kak and M. Slaney, which is also incorporated herein by reference. Exact cone beam reconstruction algorithms are also suitable for this purpose. The present invention is not limited with respect to the reconstruction algorithm that is utilized for this purpose.

The method of the present invention in accordance with the preferred embodiment will now be described with reference to FIG. 2. The first step in the process is to acquire the data, as indicated by block 11. The acquired data is stored in memory so that it can be available for use, if necessary, in retrospectively reconstructing a high resolution image of a particular region of interest. The rebinning process is then performed on the projection data, as indicated by block 12. A first reconstruction of the image is then performed using the rebinned projection data, as indicated by block 13. A process technique is then performed to identify one or more regions of interest, such as, for example, a lung nodule in a passageway of a human lung. This step, which is represented by block 14, can be performed automatically by a computer that performs, for example, a feature recognition routine, or it can be performed by a human. The reconstructed image may be displayed on the display device 9 to enable viewing by a human.

If a particular region of interest is identified, all of the projection data corresponding to the region of interest is available in the memory device to be used to retrospectively reconstruct a high resolution image of the region. The region is either identified by a human who uses an input device (e.g., a mouse, stylus, etc.) to identify a region of interest or by a computer that automatically identifies a region of interest. Once the region of interest has been identified, retrospective reconstruction is performed to produce a high resolution image of the region, as indicated by block 15. A process technique may then be performed by a human or machine to evaluate the reconstructed high resolution image, as indicated by block 16.

Therefore, a single scanning procedure is used to acquire all of the data that is needed to perform the low and high resolution reconstructions. It should be noted that it is not necessary that the method represented by the flow chart of FIG. 2 be performed on-line while the patient 6 is being imaged. The method of the present invention may be performed entirely off-line. Preferably, the method of the present invention is performed on-line in real time as the patient is being imaged. Alternatively, some of the steps may be performed on-line in real time and others may be performed off-line. For example, steps 11, 12 and 13 may be performed in real time as the patient 6 is being imaged and steps 14, 15 and 16 may be performed offline after the data acquisition process has been completed.

Figure 2:
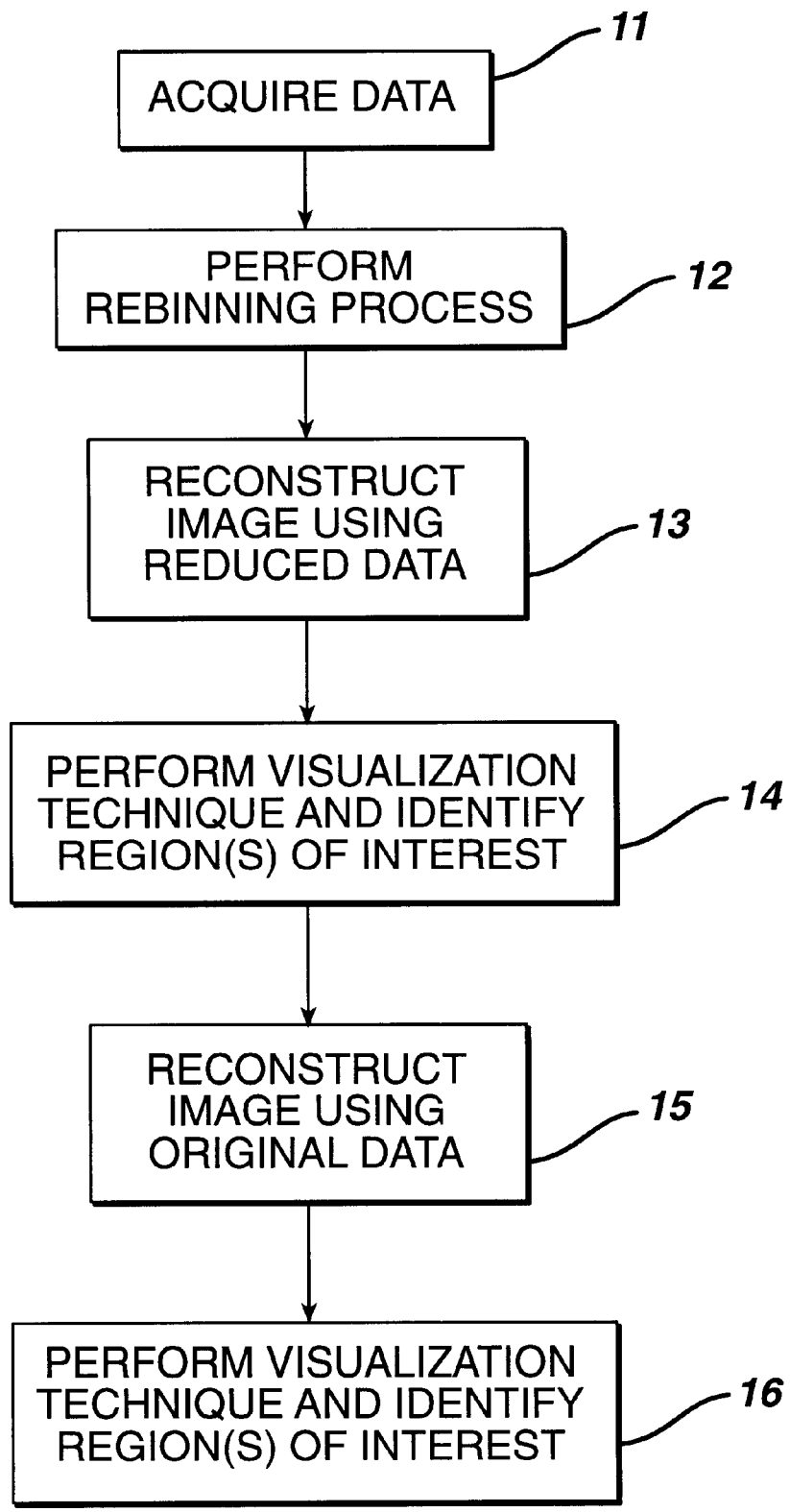
FIG. 2 is a flow chart illustrating the method of the present invention in accordance with the preferred embodiment.
Figure 3:
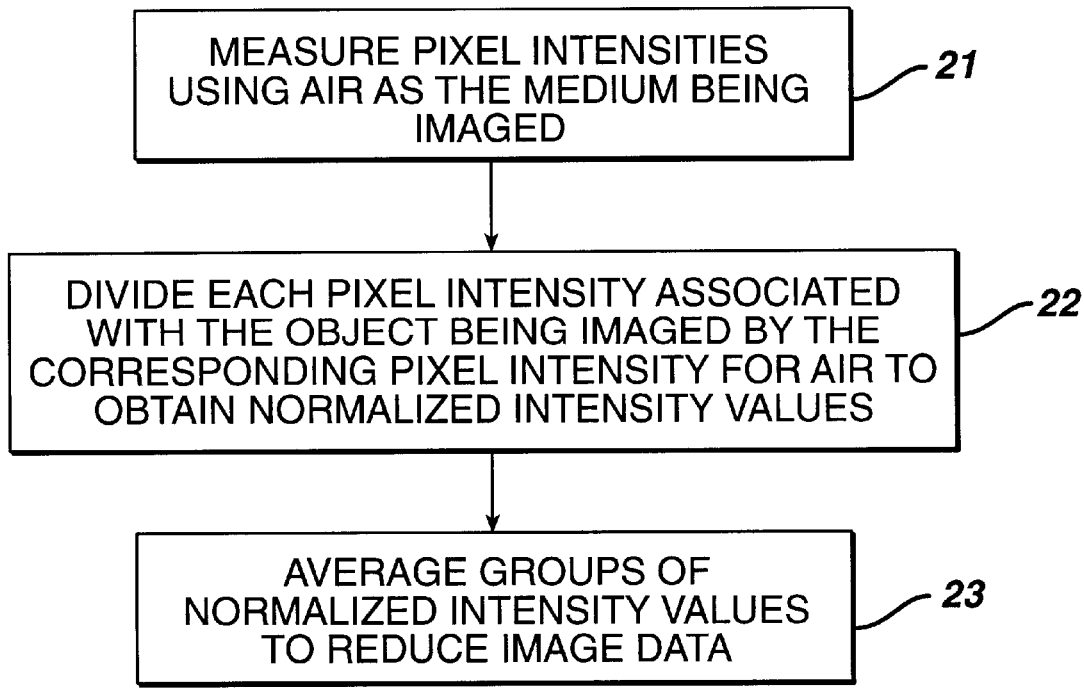
FIG. 3 is a flow chart illustrating one embodiment for performing the rebinning step of the method shown in FIG. 2.
Figure 4:
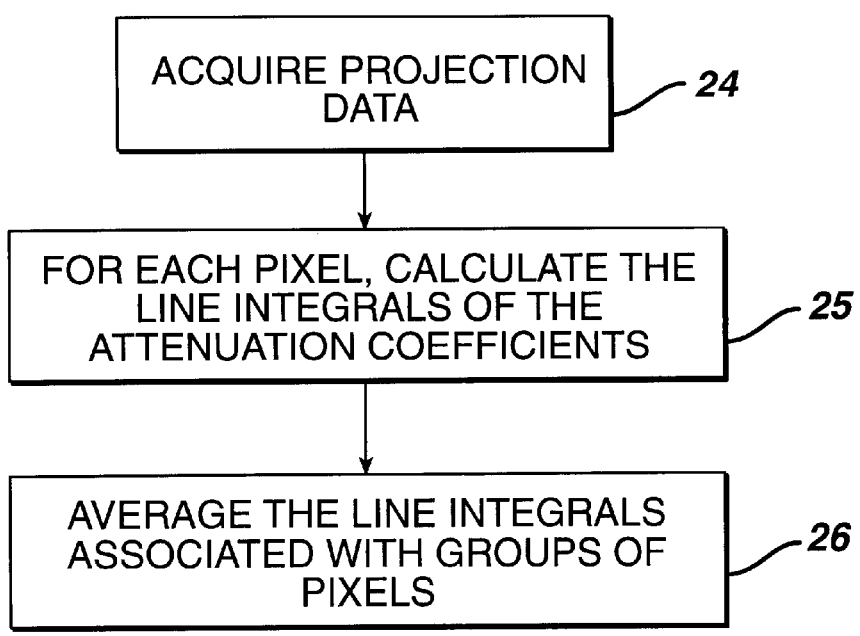
FIG. 4 is a flow chart illustrating another embodiment for performing the rebinning step of the method shown in FIG. 2.

FIG. 3 is a flow chart illustrating a first embodiment for performing the rebinning step represented by block 12 in FIG. 2. FIG. 3 is a flow chart illustrating another embodiment for performing the rebinning step represented by block 12 in FIG. 2. Ideally, all pixels of a detector have the same gain response. In practice, this may not be the case. Therefore, if rebinning were performed by simply averaging groups of pixels, non-linearities may be result that produce artifacts in reconstructed images. FIGS. 3 and 4 illustrate the maimer in which rebinning can be performed without introducing such non-linearities.

In accordance with the embodiment shown in FIG. 3, the intensity values of the pixels are normalized prior to performing the averaging step. One way to normalize the intensity values is to determine the intensity values for air, i.e., when the x-rays impinge on the detector without first passing through an object, and then divide those values into the intensity values resulting when the object is imaged. Block 21 corresponds to the step of measuring the intensity values of the pixels for air. Block 22 corresponds to the step of normalizing the intensity values by dividing each intensity values that results when the object is imaged by the respective intensity value acquired during the step represented by block 21. Once the normalized intensity values have been computed, the projection data corresponding to each radiograph is rebinned by averaging groups of normalized intensity values for groups of pixels (e.g., 2-by-2 or 4-by-4, etc.), as indicated by block 23. The rebinned data is then processed during the step represented by block 13 in FIG. 2 to reconstruct the image.

It should be noted that before the intensity values corresponding to the imaged object are normalized, baseline intensity values are subtracted from both the intensity values corresponding to air and the intensity values corresponding to the imaged object. The baseline intensity values for each pixel are obtained by measuring the intensity values when no x-rays are being projected by the x-ray source onto the detector. The image acquired by the detector in this case is commonly referred to as a "dark" or "offset" image. The intensity values associated with the dark image correspond to background noise measurements.

FIG. 4 represents another embodiment for performing the rebinning step represented by block 12 in FIG. 3. In accordance with this embodiment, line integrals of attenuation coefficients are calculated for each pixel and then groups of line integrals are averaged to thereby rebin the projection data. The first step in this process is to acquire the projection data associated with the object being imaged! as indicated by block 24. For each pixel, the line integrals of the attenuation coefficients are calculated, as indicated by block 25. Attenuation of the x-rays through the object being imaged can be modeled as an exponential function defined as: $e^{-\int U_L dL} = I/I_O$, where $I_O$, represents the intensity value of the pixel when air is the medium being imaged, I represents the intensity value of the pixel when the object 6 is being imaged, dL is the incremental length of the portion of the object 6 that the ray passes through, and $U_L$ is the attenuation coefficient.

If the natural log of both sides of this equation is taken, the line integral of the attenuation coefficients for the pixel is obtained, which corresponds to a summation of the attenuation coefficients for that pixel along a ray connecting the source and the pixel. For groups of pixels (e.g., 2-by-2, 4-by-4, etc.), the resulting summations are averaged to thereby rebin the projection data. This step of averaging the line integrals of the attenuation coefficients is represented by block 26. Once the data has been rebinned in this manner, the step represented by block 13 in FIG. 2 is performed to perform the first reconstruction.

It should be noted that obtaining the line integrals of the linear attenuation coefficients is a process that is typically done by CT systems. Therefore, the step represented by block 24 in FIG. 4 does not need to be performed as a separate step during the rebinning process. The step represented by block 24 has been illustrated as a separate step in order to clearly demonstrate one embodiment for performing the rebinning process.

It should be noted that rebinning processes other than those represented by the flow charts of FIGS. 3 and 4 can be utilized with the present invention. For example, rather than averaging groups of intensity values or line integrals of attenuation coefficients, various statistical estimation techniques can be used to estimate the intensity value of a pixel based on the intensity values of surrounding pixels. If the data were to be reduced by a factor of 4, for example, a single intensity value would be estimated based on the intensity values of 4 adjacent pixels. Those skilled in the art will understand the manner in which various known statistical estimation techniques can be utilized to perform the rebinning process.

It should be noted that the present invention has been described with respect to the embodiments and that the present invention is not limited to these embodiments. Those skilled in the art will also understand that the present invention is not limited with respect to the type of CT system with which the present invention is implemented. Those skilled in the art will understand that modifications can be made to the embodiments discussed above without deviating from the spirit and scope of the present invention.

What is claimed is:

1. An apparatus for reconstructing an image of an object from a plurality of x-ray projection images of the object, the x-ray projection images being acquired by a computed tomography (CT) system, the CT system comprising an x-ray source and a detector, the x-ray source projecting x-rays through the object, the detector detecting x-rays that pass through the object, the detector comprising a plurality of pixels, each pixel having an intensity value associated therewith, the detector generating projection data in response to the x-rays impinging thereon, the projection data corresponding to the intensity values, the apparatus comprising:

logic configured to receive the projection data generated by the detector, said logic being configured to store the projection data in memory and to perform a rebinning process on the projection data, the rebinning process reducing the projection data from a first quantity of projection data to a second quantity of projection data, the logic being configured to perform a first reconstruction of an image of the object from the second quantity of projection data and to determine whether a second reconstruction is to be performed for a particular region of interest in the first reconstructed image, wherein if the logic determines that the second reconstruction is to be performed, the logic reads a portion of the first quantity of projection data out of memory that corresponds to the particular region of interest and performs a second reconstruction of an image of the particular region of interest, wherein the second reconstruction has a higher resolution than the first reconstruction.

2. The apparatus of claim 1, wherein said logic is a computer and wherein the computer performs an automated detection routine on the first reconstructed image to determine whether the second reconstruction is to be performed, wherein if the automated detection routine detects the particular region of interest in the first reconstructed image, the computer performs the second reconstruction.

3. The apparatus of claim 1, further comprising a display device and an input device in communication with the logic, wherein the logic is a computer and wherein the computer displays the first reconstructed image on the display device so that a user can view the displayed image to identify the particular region of interest, and wherein if the user identifies a particular region of interest in the first reconstructed image with the input device, the computer performs the second reconstruction.

4. The apparatus of claim 1, wherein the reconstruction algorithm is a filtered back projection algorithm.

5. The apparatus of claim 1, wherein the rebinning process is performed by averaging normalized pixel intensity values for groups of pixels of the detector, each group of pixels comprising an equal number of pixels.

6. The apparatus of claim 1, wherein the rebinning process is performed by averaging line integrals of linear attenuation coefficients associated with each pixel.

7. The apparatus of claim 1, wherein the detector is an area detector and wherein the CT system is a volumetric CT system, the area detector comprising a plurality of rows of pixels and a plurality of columns of pixels.

8. The apparatus of claim 1, wherein said logic is a computer and wherein the computer performs an automated detection routine on the second reconstructed image to analyze the particular region of interest.

9. The apparatus of claim 1, further comprising a display device and an input device in communication with the logic, wherein the logic is a computer and wherein the computer displays the second reconstructed image on the display device so that a user can view the displayed second reconstructed image to analyze the particular region of interest.

10. The apparatus of claim 1, wherein the reconstruction algorithm is an exact cone beam algorithm.

11. A computed tomography (CT) system for reconstructing an image of an object from a plurality of x-ray projection images of the object, the x-ray projection images being acquired by the CT system, the CT system comprising:

an x-ray source, the x-ray source projecting x-rays through the object;

a detector, the detector detecting x-rays that pass through the object, the detector comprising a plurality of pixels, each pixel having a pixel value associated therewith, the detector generating projection data in response to the x-rays impinging thereon, the projection data corresponding to the intensity values; and logic receiving the projection data generated by the detector, the logic being configured to store the projection data in memory and to perform a rebinning process on the projection data, the rebinning process reducing the projection data from a first quantity of projection data to a second quantity of projection data, the logic being configured to perform a first reconstruction of an image of the object from the second quantity of projection data and to determine whether a second reconstruction is to be performed for a particular region of interest in the first reconstructed image, wherein if the logic determines that the second reconstruction is to be performed, the logic reads a portion of the first quantity of image data out of memory that corresponds to the particular region of interest and performs a second reconstruction of an image of the particular region of interest, the second reconstruction having a higher resolution than the first reconstruction.

12. The CT system of claim 11, further comprising a display device and an input device, the display device and the input device being in communication with the logic, wherein the logic is a computer and wherein the computer displays the first reconstructed image on the display device so that a user can view the displayed image to identify the particular region of interest, and wherein if the user identifies a particular region of interest in the first reconstructed image with the input device, the computer performs the second reconstruction.

13. The CT system of claim 11, wherein the reconstruction algorithm is a filtered back projection algorithm.

14. The CT system of claim 11, wherein the reconstruction algorithm is an exact cone beam algorithm.

15. The CT system of claim 11, wherein the rebinning process is performed by averaging normalized pixel intensity values for groups of pixels of the detector, each group of pixels comprising an equal number of pixels.

16. The CT system of claim 11, wherein the rebinning process is performed by averaging line integrals of linear attenuation coefficients associated with each pixel.

17. The CT system of claim 11, wherein the detector is an area detector and wherein the CT system is a volumetric CT system, the area detector comprising a plurality of rows of pixels and a plurality of columns of pixels.

18. The CT system of claim 11, wherein said logic is a computer and wherein the computer performs an automated detection routine on the second reconstructed image to analyze the particular region of interest.

19. The CT system of claim 11, further comprising a display device and an input device in communication with the logic, wherein the logic is a computer and wherein the computer displays the second reconstructed image on the display device so that a user can view the displayed second reconstructed image to analyze the particular region of interest.

20. The CT system of claim 11, wherein said logic is a computer and wherein the computer performs an automated detection routine on the first reconstructed image to determine whether the second reconstruction is to be performed, wherein if the automated detection routine detects the particular region of interest in the first reconstructed image, the computer performs the second reconstruction.

21. A method for reconstructing an image of an object from x-ray projection data, the method comprising the steps of:
  acquiring the x-ray projection data with a computed tomography (CT) system, the CT system comprising an x-ray source and a detector, the detector comprising a plurality of pixels, each pixel having an intensity value, the x-ray source projecting x-rays through an object being imaged, the detector detecting x-rays that pass through the object, the detector generating the projection data in response to the x-rays impinging thereon;
  storing the projection data in memory;
  rebinning the projection data to reduce the projection data from a first quantity of projection data to a second quantity of projection data;
  performing a first reconstruction of an image of the object from the second quantity of projection data;
  determining whether a second reconstruction is to be performed for a particular region of interest in the first reconstructed image;
    wherein if a determination is made that the second reconstruction is to be performed, reading a portion of the first quantity of projection data out of memory that corresponds to the particular region of interest and performing a second reconstruction of an image of the particular region of interest, the second reconstruction having a higher resolution than the first reconstruction.

22. The method of claim 21, further comprising the step of displaying the first reconstructed image on a display device, wherein the step of determining whether a second reconstruction is to be performed is accomplished by a user who views the displayed image to identify the particular region of interest, and wherein if the user identifies a particular region of interest in the first reconstructed image, the second reconstruction is performed.

23. The method of claim 21, wherein the reconstruction algorithm is a filtered back projection algorithm.

24. The method of claim 21, wherein the reconstruction algorithm is an exact cone beam reconstruction algorithm.

25. The method of claim 21, wherein the rebinning step is performed by averaging normalized pixel intensity values for groups of pixels of the detector, each group of pixels comprising an equal number of pixels.

26. The method of claim 21, wherein the rebinning step is performed by averaging line integrals of linear attenuation coefficients associated with each pixel.

27. The method of claim 21, wherein the detector utilized in the acquiring step is an area detector and wherein the CT system is a volumetric CT system, the area detector comprising a plurality of rows of pixels and a plurality of columns of pixels.

28. The method of claim 21, further comprising the step of:
  performing an automated detection routine on the second reconstructed image to analyze the second reconstructed image.

29. The method of claim 21, further comprising the step of displaying the second reconstructed image on a display device to enable a user to view the displayed second reconstructed image.

30. The method of claim 21, wherein the step of determining whether a second reconstruction is to be performed comprises the step of:
  performing an automated detection routine on the first reconstructed image to determine whether the second reconstruction is to be performed, wherein if the automated detection routine detects the particular region of interest in the first reconstructed image, the computer performs the second reconstruction.

31. A computer program for reconstructing an image of an object from x-ray projection data, the projection data being acquired by a computed tomography (CT) system, the CT system comprising an x-ray source and a detector, the x-ray source projecting x-rays through the object, the detector detecting x-rays that pass through the object, the detector comprising a plurality of pixels, each pixel having an intensity value associated therewith, the detector generating projection data in response to the x-rays impinging thereon, the program being embodied on a computer-readable medium, the program comprising:
  a first code segment, the first code segment acquiring the x-ray projection data generated by the detector;
  a second code segment, the second code segment storing the projection data in a memory device;
  a third code segment, the third code segment rebinning the projection data to reduce the projection data from a first quantity of projection data to a second quantity of projection data;
  a fourth code segment, the fourth code segment performing a first reconstruction of an image of the object from the second quantity of projection data;
  a fifth code segment, the fifth code segment determining whether a second reconstruction is to be performed for a particular region of interest in the first reconstructed image;
  a sixth code segment, wherein if a determination is made that the second reconstruction is to be performed, the sixth code segment obtains a portion of the first quantity of projection data stored in the memory device that corresponds to the particular region of interest and performs a second reconstruction of an image of the particular region of interest, the second reconstruction having a higher resolution than the first reconstruction.

32. The computer program of claim 31, wherein the first and second reconstructions are performed using a filtered back projection algorithm.

33. The computer program of claim 31, wherein the first and second reconstructions are performed using an exact cone beam reconstruction algorithm.

34. The computer program of claim 31, wherein the third code segment rebins the projection data by averaging normalized pixel intensity values for groups of pixels of the detector, each group of pixels comprising an equal number of pixels.

35. The computer program of claim 31, wherein the third code segment rebins the projection data by averaging line integrals of linear attenuation coefficients associated with each pixel.

36. The computer program of claim 31, wherein the detector is an area detector and wherein the CTf system is a volumetric CT system, the area detector comprising a plurality of rows of pixels and a plurality of columns of pixels.

37. The computer program of claim 31, wherein the fifth code segment determines whether the second reconstruction is to be performed by performing an automated detection routine on the first reconstructed image, wherein if the automated detection routine detects the particular region of interest in the first reconstructed image, the computer performs the second reconstruction.

* * * * *